(12) United States Patent
Falligant et al.

(10) Patent No.: US 7,886,780 B2
(45) Date of Patent: Feb. 15, 2011

(54) METHOD AND APPARATUS FOR PREVENTING DRUG RESERVOIR OVERFILL

(75) Inventors: John C. Falligant, Edgerton, WI (US); Steven Alan Jandl, Lodi, WI (US); Brian David Paap, McFarland, WI (US)

(73) Assignee: General Electric Company, Schenectady, NY (US)

( * ) Notice: Subject to any disclaimer, the term of this patent is extended or adjusted under 35 U.S.C. 154(b) by 991 days.

(21) Appl. No.: 11/694,279

(22) Filed: Mar. 30, 2007

(65) Prior Publication Data
US 2008/0236576 A1   Oct. 2, 2008

(51) Int. Cl.
*B65B 1/30* (2006.01)
*F16K 31/18* (2006.01)
*A61M 15/00* (2006.01)

(52) U.S. Cl. .............................. 141/198; 141/7; 141/18; 141/95; 141/366; 137/413; 128/203.19

(58) Field of Classification Search ................ 141/2, 141/18, 94, 95, 98, 198, 363–366; 128/203.19; 137/101.27, 122, 413
See application file for complete search history.

(56) References Cited

U.S. PATENT DOCUMENTS

| | | | |
|---|---|---|---|
| 3,789,865 A * | 2/1974 | Borman ....................... 137/122 |
| 3,873,806 A * | 3/1975 | Schossow .................... 392/402 |
| 5,381,838 A * | 1/1995 | Watanabe et al. ........... 141/198 |
| 5,456,595 A * | 10/1995 | Henderson ..................... 431/2 |
| 5,470,511 A * | 11/1995 | Laybourne et al. ............ 261/55 |
| 5,758,640 A | 6/1998 | Kamppari et al. |
| 6,138,672 A | 10/2000 | Kankkunen |
| 6,745,800 B1 | 6/2004 | Sansom |
| 7,287,557 B2 * | 10/2007 | Bunke et al. .................. 141/95 |

* cited by examiner

*Primary Examiner*—Timothy L Maust (57) ABSTRACT

A reservoir for an anesthetic vaporizer is disclosed herein. The reservoir includes an open interior and a high-pressure channel in communication with the open interior. The high-pressure channel is configured to transfer an anesthetic agent from a storage container into the open interior when a pressure level within the storage container exceeds a pressure level within the open interior. The reservoir also includes a low-pressure channel in communication with the open interior. The low-pressure channel is configured to transfer the anesthetic agent from the storage container into the open interior when the pressure level within the storage container is less than or approximately equal to the pressure level within the open interior. The low-pressure channel and the high-pressure channel are configured to prevent the open interior from being overfilled with the anesthetic agent under conditions wherein the pressure level within the storage container exceeds the pressure level within the open interior.

18 Claims, 6 Drawing Sheets

METHOD AND APPARATUS FOR PREVENTING DRUG RESERVOIR OVERFILL

FIELD OF THE INVENTION

The present disclosure generally relates to method and apparatus configured to prevent the drug reservoir portion of an anesthetic vaporizer from being overfilled with anesthetic agent.

BACKGROUND OF THE INVENTION

During the supply of anesthesia, the gaseous anesthetic agent inhaled by the patient is generally formed of oxygen, nitrogen, nitrous oxide and an inhalation anesthetic agent. Inhalation anesthetics are typically in liquid form at administration temperatures, and an anesthetic vaporizer is implemented to convert the liquid into gas. Anesthetic vaporizers have a drug reservoir for storing the supply of the agent to be vaporized. The vaporized anesthetic is administered for the patient to inhale by means of a carrier gas flow.

Vaporizer reservoirs are provided with fill conduits and valves by way of which inhalation liquids may be added to the container or, when necessary, drained therefrom. Liquid is added to the vaporizer reservoir by either a filling device that is specifically designed for the anesthetic agent or by directly pouring the anesthetic agent into a filling hopper. It is a characteristic of the filling device that it can only be fixed to the storage container for a desired, single type of an anesthetic liquid to be transferred to the vaporizer.

The filling device incorporates a liquid flow conduit and a gas flow conduit. The filling of the drug reservoir for the anesthetic vaporizer is based on the exchange of volume in the vaporizer and the storage container for the anesthetic liquid. When the anesthetic liquid flows into the vaporizer, an equivalent volume of gas flows out of the vaporizer and back into the storage container. Correspondingly, when anesthetic liquid flows out of the storage container, an equivalent volume of gas flows back into the storage container. The filling of the vaporizer typically stops if the replacement gas flow is exhausted or blocked.

It is essential for the operation of the vaporizer that the vaporizer drug reservoir is not filled over a maximum limit. If the vaporizer reservoir is overfilled, the result may be that an overly high dose of anesthetic agent is delivered. Otherwise, depending upon the vaporizer, an overfilled reservoir may trigger a shutdown and could thereby cause the patient to prematurely awaken. One problem with conventional anesthetic vaporizers is that, under certain circumstances, their drug reservoirs can be overfilled. Some exemplary circumstances under which the drug reservoirs can overfill include situations wherein the anesthetic vaporizers are tilted or when they are being filled with an anesthetic agent having a high vapor pressure.

SUMMARY OF THE INVENTION

The above-mentioned shortcomings, disadvantages and problems are addressed herein which will be understood by reading and understanding the following specification.

In an embodiment, a reservoir for an anesthetic vaporizer includes an open interior and a high-pressure channel in communication with the open interior. The high-pressure channel is configured to transfer an anesthetic agent from a storage container into the open interior when a pressure level within the storage container exceeds a pressure level within the open interior. The reservoir also includes a low-pressure channel in communication with the open interior. The low-pressure channel is configured to transfer the anesthetic agent from the storage container into the open interior when the pressure level within the storage container is less than or approximately equal to the pressure level within the open interior. The low-pressure channel and the high-pressure channel are configured to prevent the open interior from being overfilled with the anesthetic agent under conditions wherein the pressure level within the storage container exceeds the pressure level within the open interior.

In another embodiment, a reservoir for an anesthetic vaporizer includes an open interior and a low-pressure channel in communication with the open interior. The low-pressure channel is configured to transfer an anesthetic agent from a storage container to the open interior. The reservoir also includes a low-pressure device operatively connected to the low-pressure channel. The low-pressure device is configured to selectively occlude the low-pressure channel. The reservoir also includes a high-pressure channel in communication with the open interior. The high-pressure channel is configured to transfer the anesthetic agent from the storage container to the open interior. The reservoir also includes a high-pressure device operatively connected to the high-pressure channel. The high-pressure device is configured to selectively occlude the high-pressure channel. The low-pressure device and the high-pressure device are configured to prevent the open interior from being overfilled with the anesthetic agent under conditions wherein a pressure level within the storage container exceeds a pressure level within the open interior.

In another embodiment, a method for filling a drug reservoir of an anesthetic vaporizer includes providing a low-pressure channel and a high-pressure channel in communication with an open interior. The method also includes transferring anesthetic agent from a storage container, through the low-pressure channel and into the open interior when a pressure level within the storage container is less than or approximately equal to a pressure level within the open interior. The method also includes transferring anesthetic agent from the storage container, through the high-pressure channel and into the open interior when the pressure level within the storage container exceeds the pressure level within the open interior portion. The method also includes occluding the high-pressure channel when the anesthetic agent within the open interior reaches a predetermined level.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
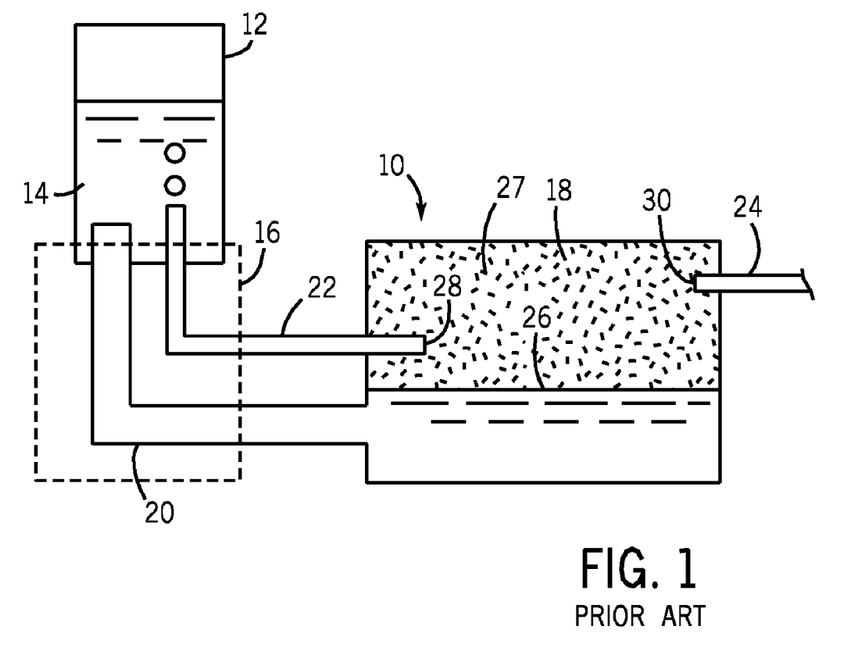
FIG. 1 is a schematic illustration of a prior art filling arrangement between a drug reservoir of an anesthetic vaporizer and an anesthetic agent storage container.

Referring to FIG. 1, a conventional filling arrangement is schematically depicted. The filling arrangement of FIG. 1 includes a drug reservoir 10 for an anesthetic vaporizer (not shown) and a storage container 12 containing a supply of an anesthetic agent 14. A filler 16 is positioned between the storage container 12 and the drug reservoir 10 to provide a conduit between the container 12 and the open interior 18 of the reservoir 10. In the filling arrangement of FIG. 1, the filling system is closed and the anesthetic agent 14 is not allowed to vaporize to external atmosphere. The filler 16 includes a liquid tube 20 extending from the storage container 12 to the open interior 18 of the reservoir 10. A gas tube 22 also extends from the container 12 to the open interior 18 of the drug reservoir 10.

Liquid anesthetic agent 26 within the open interior 18 of the drug reservoir 10 is converted to vaporized anesthetic agent 27 in a known manner. The vaporized anesthetic agent 27 is passed through the inlet end 30 of the discharge tube 24 and administered to a patient (not shown). As liquid anesthetic agent 26 is converted to vaporized anesthetic agent 27 and administered to the patient, the liquid anesthetic agent 26 is depleted and must be refilled. The following section will describe the process of refilling the drug reservoir 10 with the anesthetic agent 14.

As the drug reservoir 10 is being filled with anesthetic agent 14, gas (e.g., vaporized anesthetic agent 27) travels from the open interior 18 through the gas tube 22 and displaces the anesthetic agent 14 within the storage container 12. The displaced anesthetic agent 14 is passed through the liquid tube 20 and into the open interior 18 of the drug reservoir 10. This process generally continues until the level of the liquid anesthetic agent 26 within the open interior 18 rises above the inlet end 28 of the gas tube 22 (as shown in FIG. 2).

Figure 2:
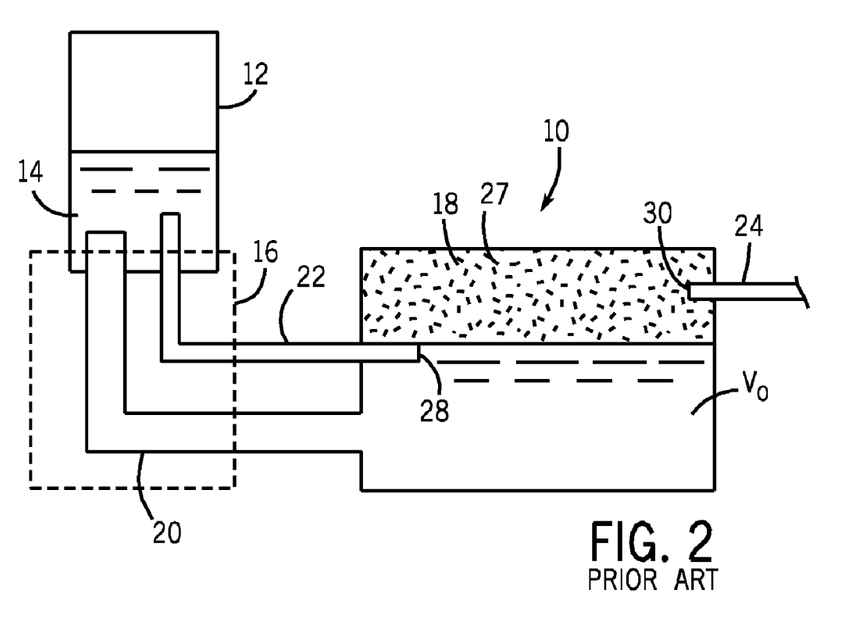
FIG. 2 is a schematic illustration depicting the prior art drug reservoir of FIG. 1 filled with liquid anesthetic agent.

Referring to FIG. 2, a full drug reservoir 10 is shown. For purposes of this disclosure, the drug reservoir 10 is considered full when it contains the design intent optimal volume Vo of anesthetic agent 26. It can be seen that the optimal volume Vo of anesthetic agent 26 is enough to just cover the inlet end 28 of the gas tube 22 when the drug reservoir 10 is generally horizontal or level (i.e., not tilted). When the inlet end 28 is covered, and when the pressure level of the anesthetic agent 14 in the storage container 12 is approximately equal to the pressure level of the anesthetic agent 26 in the drug reservoir 10, filling of the drug reservoir 10 is automatically halted.

Figure 3:
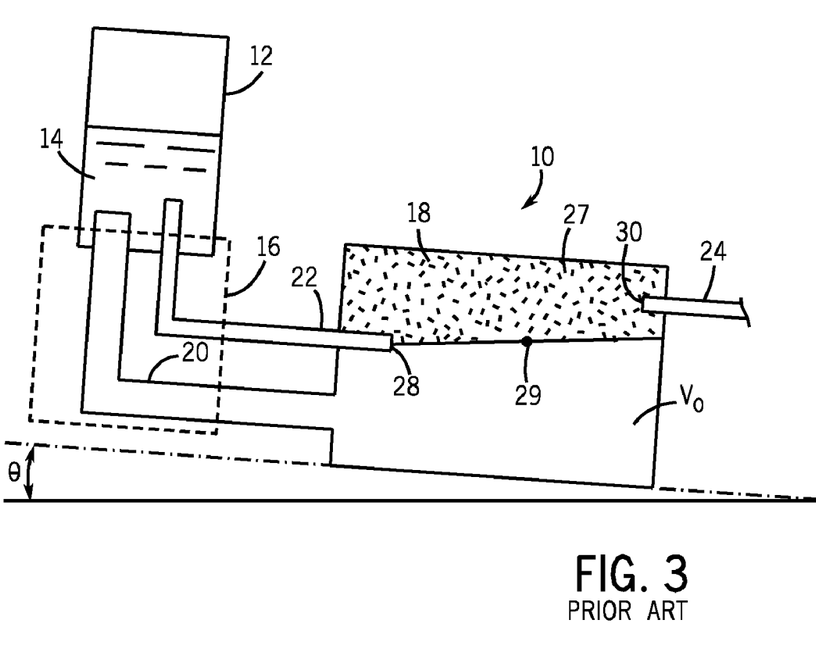
FIG. 3 is a schematic illustration depicting the prior art drug reservoir of FIG. 1 that is tilted and therefore prone to overfilling.

Referring to FIG. 3, the conventional drug reservoir 10 is shown tilted at an angle θ and with the design intent optimal volume Vo of anesthetic agent 26. It can be seen that, even though the drug reservoir 10 contains the optimal volume Vo of liquid anesthetic agent 26, the tilt angle θ exposes the inlet end 28 of the gas tube 22. Therefore, as a result of the tilt angle θ, the conventional drug reservoir 10 can continue to accept additional anesthetic agent 26 such that the drug reservoir 10 is overfilled (i.e., the optimal volume Vo is exceeded).

The point 29 is referred to as the "pitch center" of the liquid anesthetic agent 26 and is defined as the point at which the level of anesthetic agent 26 remains generally constant within a predefined range of drug reservoir 10 tilt angles (e.g., +/−20 degrees). As shown in FIG. 3, the point 29 represents the pitch center of the anesthetic agent 26 as measured along the length of the drug reservoir 10. It should also be appreciated that the point 29 may additionally represent the pitch center of the anesthetic agent 26 as measured along the width (not shown) of the drug reservoir 10.

Figure 4:
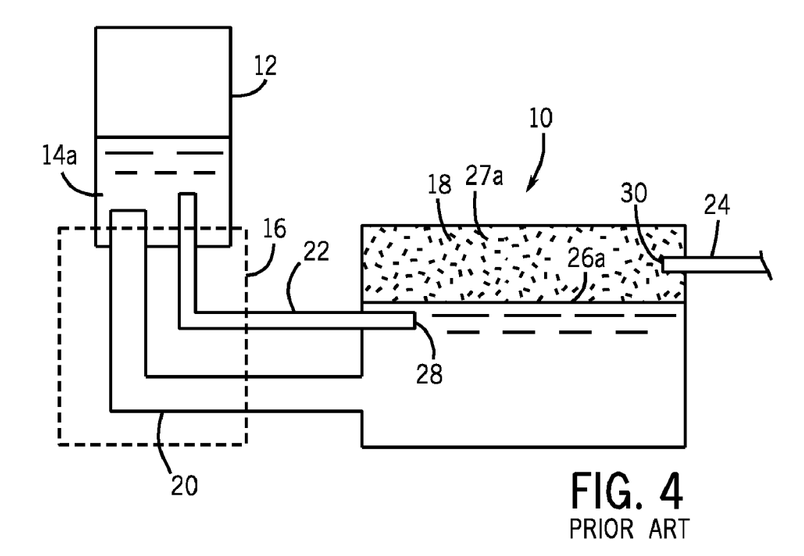
FIG. 4 is a schematic illustration depicting the prior art drug reservoir of FIG. 1 that is overfilled with an anesthetic agent having a high vapor pressure.

Referring to FIG. 4, the conventional drug reservoir 10 is shown containing a liquid anesthetic agent 26a having a high vapor pressure such as, for example, Desflurane. Unlike many other anesthetic agents, Desflurane boils at room temperature. When the anesthetic liquid 14a begins to boil, the pressure inside the storage container 12 increases. If the temperature of the anesthetic agent 14a in the storage container 12 exceeds the temperature of the anesthetic agent 26a contained within the drug reservoir, the pressure in the storage container 12 can cause the level of the anesthetic agent 26a within the reservoir 10 to continue to rise even though the inlet end 28 of the gas tube is covered and no vapor is flowing back into the supply container 12. Therefore, the conventional drug reservoir 10 may become overfilled when a liquid anesthetic agent 26a having a high vapor pressure such as, for example, Desflurane is implemented.

The prior art filling system shown in FIGS. 1-4 works properly to prevent reservoir overfill when it is level (i.e., not tilted), and when it is used with most conventional anesthetic drugs such as Enflurane, Halothane, Isoflurane and Sevoflurane. For these typical anesthetic agents, the pressure difference over a small temperature change is relatively small. For example, the pressure rise of Sevoflurane from 21° C. to 23° C. is approximately 15 mmHg. However, in the case of the anesthetic agent Desflurane, the pressure difference for a small temperature change is much larger due to its relatively low boiling point. As an example, the pressure rise of Desflurane for a temperature change from 21° C. to 23° C. is approximately 65 mmHg, which is more than four times greater than Sevoflurane. Therefore, if the temperature of the Desflurane within a storage container is slightly greater than the temperature of the Desflurane within a drug reservoir, the resultant pressure differential can cause the drug reservoir to overfill. The filling system 32 described in detail hereinafter has been developed based upon this characteristic of Desflurane.

Figure 5:
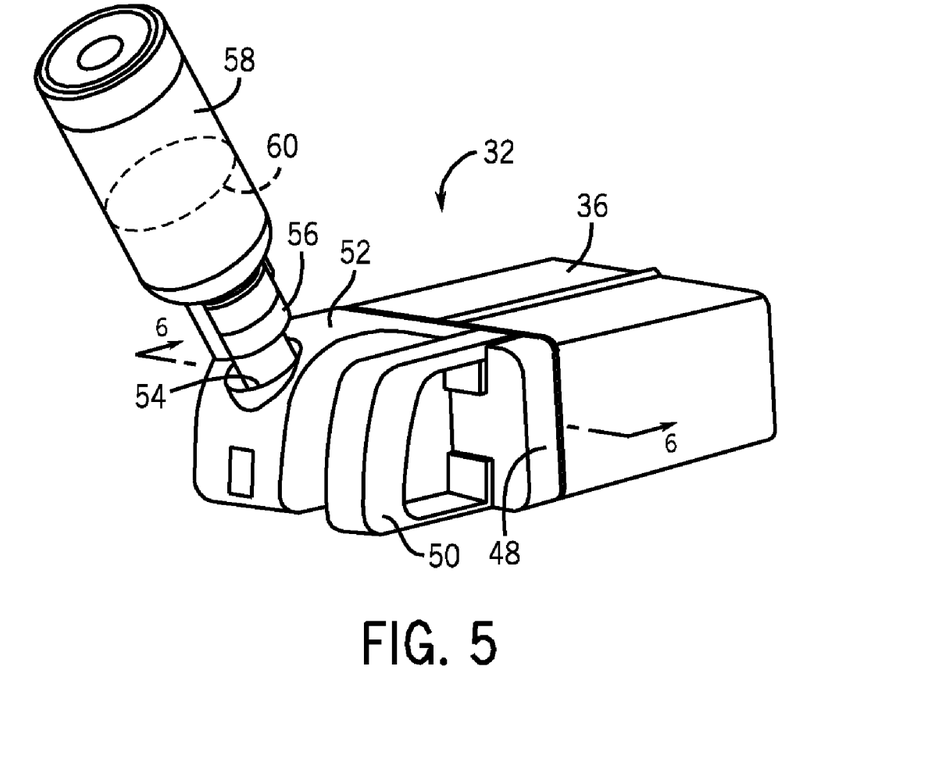
FIG. 5 is a perspective view illustrating a filling system in accordance with an embodiment.

Referring to FIG. 5, the filling system 32 is shown in accordance with an embodiment. The filling system 32 shown includes a drug reservoir 36 that is removable from a vaporizer (not shown) such that a supply of an anesthetic agent can be delivered to a patient (not shown). Different types of anesthetic agents can be supplied to the vaporizer by simply removing the drug reservoir 36 and replacing it with a different drug reservoir containing a different anesthetic agent. The drug reservoir 36 will hereinafter be described in accordance with an exemplary embodiment as containing Desflurane, however it should be understood that the filling system 32 and drug reservoir 36 could be utilized with other types of anesthetic agent while operating within the scope of the present disclosure.

The drug reservoir 36 defines an open interior 38 that receives a stored supply of anesthetic agent 40. The drug reservoir 36 has a discharge opening 42 in communication with the open interior 38. The discharge opening 42 is defined by the back wall 44 and is adapted to receive a vaporizer discharge tube 46. Typically, the reservoir 36 plugs into the vaporizer (not shown) such that the vaporizer discharge tube 46 is received within the discharge opening 42 and forms a gas-tight seal for the delivery of anesthetic vapor to a patient.

Referring back to FIG. 5, a front cover 48 having a handle 50 is attached to the drug reservoir 36. The front cover 48 encloses a filling device 52 having a filler port 54. The filler port 54 receives a bottle adapter 56 on the anesthetic storage container 58. The anesthetic storage container 58 includes a supply of an anesthetic agent 60 such as, for example, Desflurane. The interaction between the bottle adapter 56 and the filler port 54 allows only a single type of anesthetic agent to be dispensed into the drug reservoir 36. A different reservoir, including a specific filler port, is required for dispensing each different type of anesthetic agent. In this manner, the improper delivery of an anesthetic agent can be eliminated.

Figure 6:
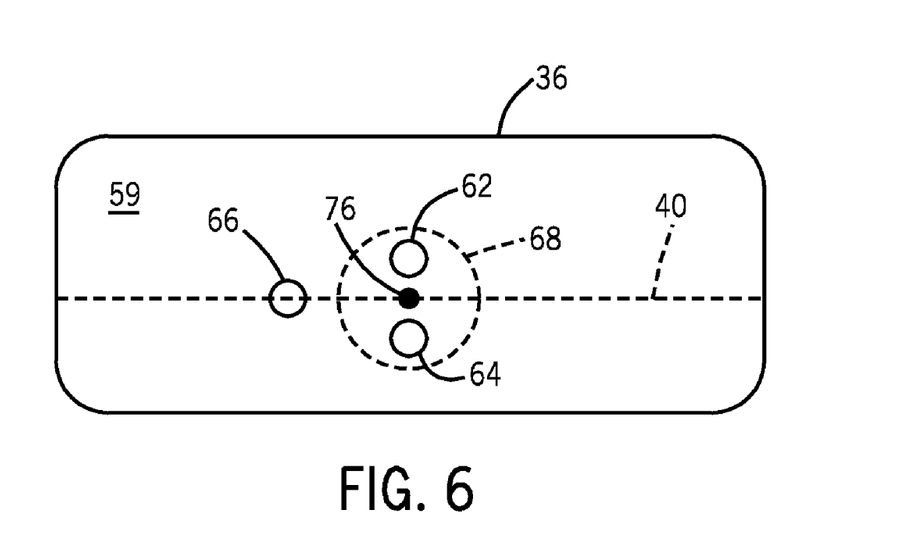
FIG. 6 is a sectional view of the filling system of FIG. 5.

Referring to FIG. 6, a sectional view taken through section 6-6 (shown in FIG. 5) illustrates the drug reservoir 36 near its interface with the front cover 48 (shown in FIG. 5). The drug reservoir 36 includes a front surface 59 at least partially defining a low-pressure vapor return port 62, a low-pressure channel 64 and a high-pressure channel 66. The high-pressure channel 66 is generally implemented to fill the drug reservoir 36 when the pressure level in the storage container 58 (shown in FIG. 5) exceeds the pressure level in the drug reservoir 36 by a predetermined amount (e.g., by an amount known to cause overfilling in conventional systems such as those described in FIGS. 1-4). This condition can occur, for example, when implementing a liquid anesthetic agent having a high vapor pressure such as Desflurane, and when the temperature of the storage container 58 exceeds the temperature of the drug reservoir 36. The low-pressure channel 64 is generally implemented to fill the drug reservoir 36 when the pressure level in the storage container 58 is less than or approximately equal to the pressure level in the drug reservoir 36.

Still referring to FIG. 6, the dashed line represents the anesthetic agent 40 within the drug reservoir 36. The point 76 represents the pitch center of the anesthetic agent 40 as measured along the width of the drug reservoir 36. As previously described, the pitch center is defined as the point at which the level of anesthetic agent 40 remains generally constant within a predefined range of drug reservoir 36 tilt angles (e.g., +/−20 degrees). The dashed circle 68 represents the portion of the front surface 60 that is engaged by a valve seal 84 described in detail hereinafter.

Referring to FIGS. 7-10, a schematic illustration of the filling system 32 is shown in accordance with an embodiment. The storage container 58 is shown mounted to the filling device 52, which in turn is attached to the drug reservoir 36. The filling device 52 defines a single filling conduit 70 that provides a flow passageway for both liquid and vapor to pass between the storage container 58 and the drug reservoir 36. The filling conduit 70 includes a first end 72 in communication with the low-pressure vapor return port 62, the low-pressure channel 64 and the high-pressure channel 66, and a second end 74 in communication with the anesthetic storage container 58.

Figure 7:
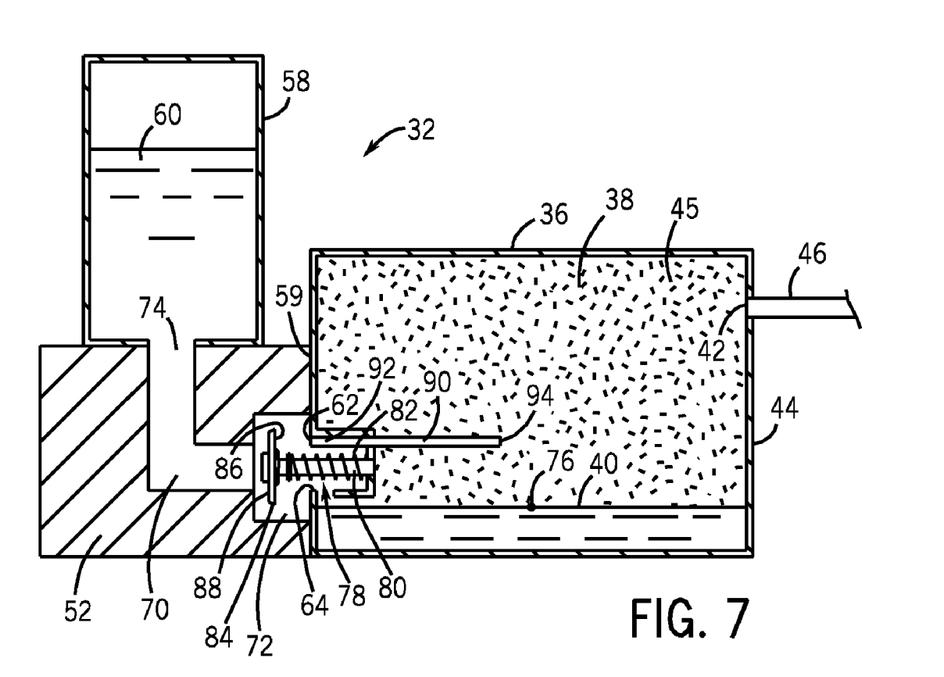
FIG. 7 is a schematic side view of a filling system including a low-pressure valve assembly in the open position.
Figure 8:
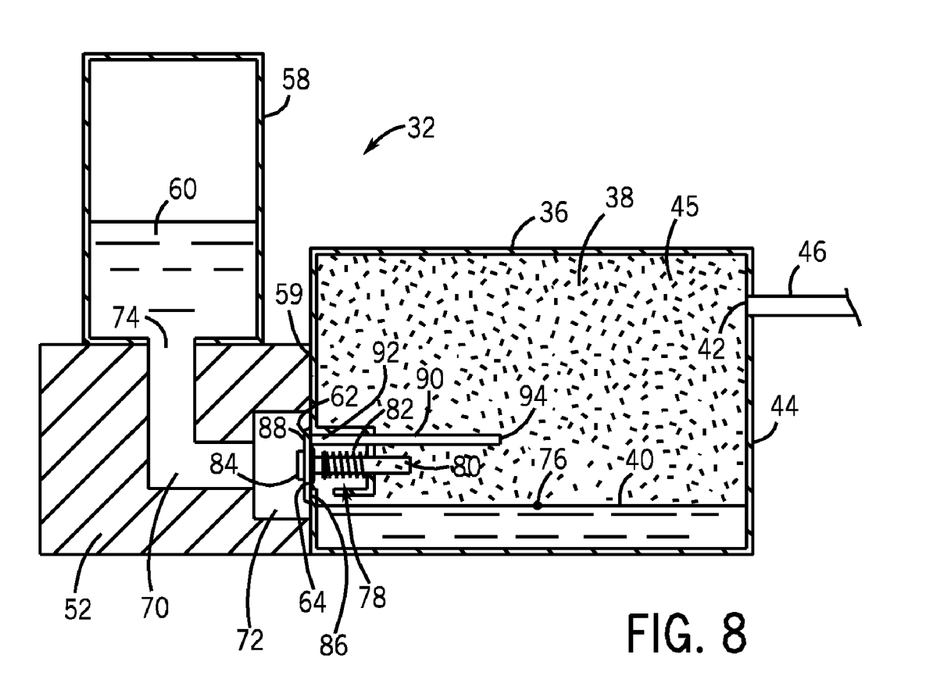
FIG. 8 is a schematic side view of a filling system including a low-pressure valve assembly in the closed position.

With reference to FIGS. 7-8, the following section will describe the operation of the low-pressure vapor return port 62 and the low-pressure channel 64. The low-pressure channel 64 is configured to transfer anesthetic agent 60 from the storage container 58 to the drug reservoir 36 under conditions wherein the pressure level within the storage container 58 does not appreciably exceed the pressure level within the drug reservoir 36. If the pressure level within the storage container 58 does appreciably exceed the pressure level within the drug reservoir 36, the low-pressure channel 64 (and the low-pressure vapor return port 62) are automatically occluded by a low-pressure valve assembly 78 such that the drug reservoir 36 can only be filled through the high-pressure channel 66 (shown in FIGS. 9-10). The low-pressure valve assembly 78 includes a valve shaft 80, a valve spring 82 and a valve seal 84.

The valve seal 84 is attached to an end portion of the valve shaft 80. When the valve seal 84 is extended away from the front surface 59 of the drug reservoir 36 as shown in FIG. 7, the valve assembly 78 is in its "open position". When the valve assembly 78 is in its open position, anesthetic agent 60 is transferable from the storage container 58 through the low-pressure channel 64 in order to fill the drug reservoir 36. When the valve seal 84 is brought into contact with the front surface 59 of the drug reservoir 36 as shown in FIG. 8, the valve assembly 78 is in its "closed position". When the valve assembly 78 is in its closed position, the low-pressure vapor return port 62 and the low-pressure channel 64 are both occluded.

The valve seal 84 includes a first surface 86 generally facing toward the drug reservoir 36, and a second surface 88 generally facing away from the drug reservoir 36. The pressure in the drug reservoir 36 applies a force to the first surface 86 of the valve seal 84 that is proportional to the reservoir pressure level. Similarly, the pressure in the storage container 58 applies a force to the second surface 88 of the valve seal 84 that is proportional to the storage container pressure level. Therefore, when the pressure in the storage container 58 exceeds the pressure in the drug reservoir 36 by an amount necessary to overcome the valve spring 82, the valve seal 84 is translated into engagement with the front surface 59 of the drug reservoir 36 such that the low-pressure vapor return port 62 and the low-pressure channel 64 are both occluded.

The valve spring 82 generally circumscribes at least a portion of the valve shaft 80, and is configured to bias the valve assembly 78 into its open position shown in FIG. 7. The valve spring 82 has a predetermined spring constant that is selectable to establish the pressure differential required to close the valve assembly 78. The spring constant is selected such that the valve spring 82 compresses by an amount necessary to close the valve assembly 78 when the pressure in the storage container 58 exceeds the pressure in the drug reservoir 36 by a predetermined amount. The predetermined amount may, for example, be that which has been observed to cause overfilling in conventional systems such as those described in FIGS. 1-4.

Still referring to FIGS. 7-8, the filling system 32 also may include a low-pressure vapor return tube 90. The low-pressure vapor return tube 90 defines an outlet end 92 coupled the low-pressure vapor return port 62, and an inlet end 94 in communication with the open interior 38 of the drug reservoir 36.

According to one embodiment, the inlet end 94 of the low-pressure vapor return tube 90 extends to the pitch center 76 of the anesthetic agent 40 as measured along the length of the drug reservoir 36. As shown in FIG. 6, the low-pressure vapor return port 62 is also aligned with the pitch center 76 of the anesthetic agent 40 as measured along the width of the drug reservoir 36. As previously described, the pitch center is defined as the point at which the level of anesthetic agent 40 remains generally constant within a predefined range of drug reservoir 36 tilt angles (e.g., +/−20 degrees). Advantageously, aligning the low-pressure vapor return port 62 and the low-pressure vapor return tube 90 with the pitch center 76 in the manner described ensures that the low-pressure vapor return tube 90 will become occluded when the reservoir 36 is full, and can thereby prevent reservoir overfill even if the reservoir 36 is tilted.

Figure 9:
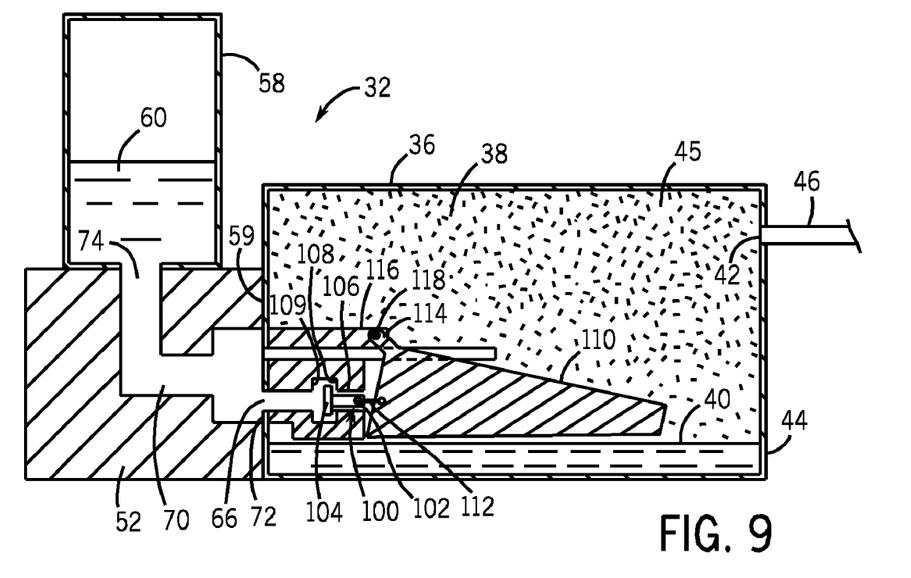
FIG. 9 is a schematic side view of a filling system including a high-pressure valve assembly in the open position.
Figure 10:
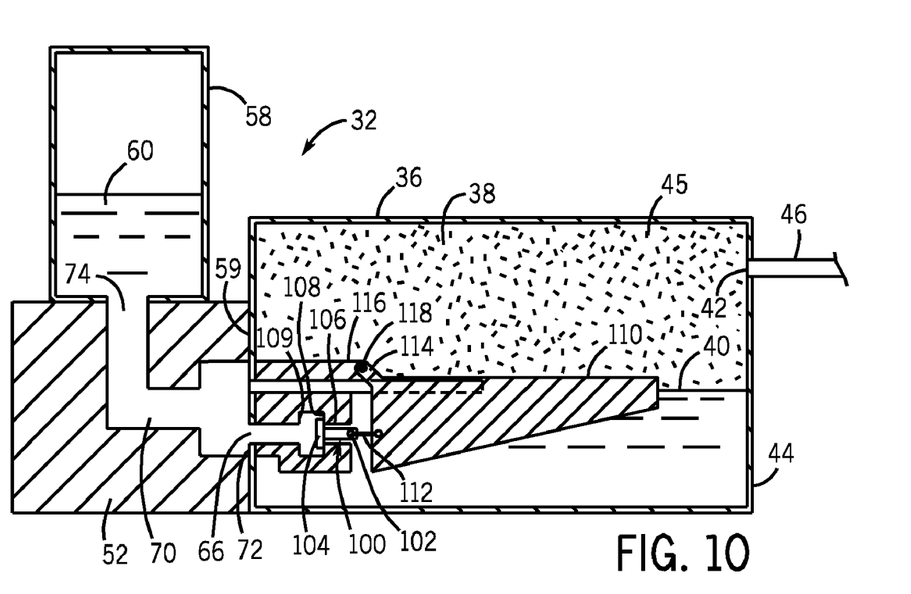
FIG. 10 is a schematic side view of a filling system including a high-pressure valve assembly in the closed position.

With reference to FIGS. 9-10, the following section will describe the operation of the high-pressure channel 66. The high-pressure channel 66 is configured to transfer anesthetic agent 60 from the storage container 58 to the drug reservoir 36 under conditions wherein the pressure level within the storage container 58 exceeds the pressure level within the drug reservoir 36 by a predetermined amount (e.g., two psi). When the drug reservoir 36 is being filled via the high-pressure channel 66 the vapor 45 within the drug reservoir 36 is compressed rather than being transferred back to the storage container 12. This compression of the vapor 45 increases the pressure level within the drug reservoir 36. If the pressure within the drug reservoir 36 becomes high enough, the resultant force applied to the first surface 86 of the valve seal 84 (shown in FIG. 8) can re-open the low-pressure valve assembly 78 (shown in FIG. 8) such that the drug reservoir 36 continues filling through the low-pressure channel 64 (shown in FIG. 7).

A high-pressure valve assembly 100 is operable to automatically regulate fluid flow through the high-pressure channel 66 in direct response to the changing level of the anesthetic agent 40 within the drug reservoir 36. When the level of the anesthetic agent 40 reaches a desired level, the high-pressure valve assembly 100 blocks the high-pressure channel 66 as will be described in detail hereinafter. The high-pressure valve assembly 100 includes a valve shaft 102 and a valve seal 104 attached thereto.

The high-pressure channel 66 includes a reduced diameter portion 106 defining a shoulder 108. When the valve seal 104 is extended away from the shoulder 108 as shown in FIG. 9, the high-pressure valve assembly 100 is in its "open position". When the high-pressure valve assembly 100 is in its open position, anesthetic agent 60 can pass through the high-pressure channel 66 in order to fill the drug reservoir 36. When the valve seal 104 is brought into contact with the shoulder 108 as shown in FIG. 10, the high-pressure valve assembly 100 is in its "closed position". When the high-pressure valve assembly 100 is in its closed position, the high-pressure channel 66 is occluded.

The valve shaft 102 is coupled to a float 110 with a member 112. The float 110 is disposed within the open interior 38 of the drug reservoir 36, and is comprised of a buoyant material adapted to float on the stored supply of anesthetic agent 40. The float 110 includes a pivot arm 114 pivotably connected to a protrusion 116 at the connection point 118. The float 110 is allowed to pivot about the connection point 118 such that the float 110 can rise and fall along with the level of the anesthetic agent 40 contained within the reservoir 36.

When the level of anesthetic agent 40 within the reservoir 36 is sufficiently low, the float 110 pivots about the connection point 118 in a downward direction under the influence of gravity as shown in FIG. 9. The downward rotation of the float 110 applies a generally horizontal force tending to push the member 112 and the valve shaft 102 attached thereto. This generally horizontal force pushing on the valve shaft 102 maintains separation between the valve seal 104 and the shoulder 108 such that the high-pressure valve assembly 100 remains in its open position and anesthetic agent 60 is transferable through the high-pressure channel 66.

When the level of anesthetic agent 40 within the reservoir 36 increases, the float 110 rises and pivots about the connection point 118 thereby applying a generally horizontal force tending to pull the member 112 and the valve shaft 102 attached thereto. As the float 110 continues to rise, the generally horizontal force applied to the valve shaft 102 draws the valve seal 104 toward the shoulder 108. When the float 110 reaches a predetermined level indicative of a full reservoir 36, the float 110 pulls the valve seal 104 into engagement with the shoulder 108 such that the high-pressure channel 66 is occluded. Therefore, reservoir overfill can be prevented even if the pressure within the anesthetic storage container 58 exceeds the pressure within the drug reservoir 36.

According to one embodiment, the center of buoyancy (not shown) of the float 110 is positioned to align with the pitch center 76 (shown in FIG. 7) of the anesthetic agent 40 such that, as the float 110 rises, the float's center of buoyancy passes vertically through the pitch center 76. In this manner, the operation of the float 110 is minimally affected by reservoir tipping or tilt.

Figure 11:
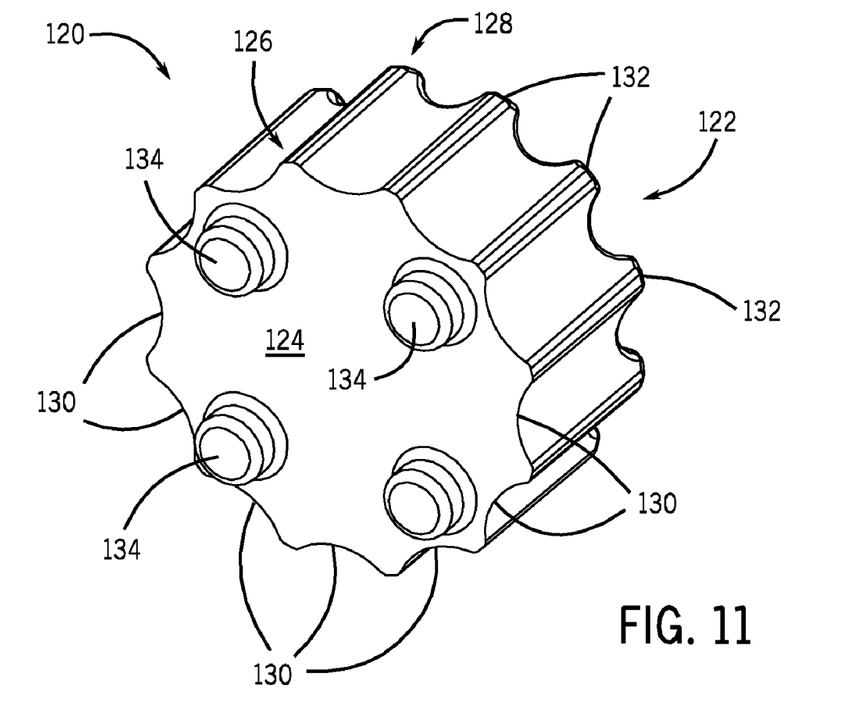
FIG. 11 is a perspective view of a routing device in accordance with an embodiment.

Referring to FIG. 11, a routing device 120 may be disposed within the high-pressure channel 66 to direct the flow of anesthetic fluid 60. The routing device 120 is generally cylindrical and defines a hollow interior 122. The routing device 120 includes an end cap 124 disposed at a first end portion 126, and a generally opposite open end portion 128. The outer periphery of the routing device 120 defines a plurality of channels 130 extending in an axial direction. The routing device 120 also includes a first plurality of protrusions 132 axially extending from the open end portion 128, and a second plurality of protrusions 134 axially extending from the end cap 124.

Figure 12:
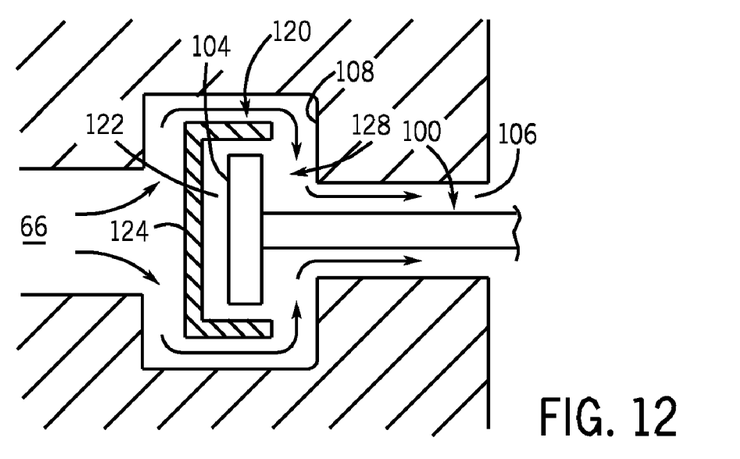
FIG. 12 is a schematic side view of the routing device of FIG. 11 and the high-pressure valve assembly of FIGS. 9-10.

Referring to FIGS. 9-12, the routing device 120 is disposed within the high-pressure channel 66 such that the first plurality of protrusions 132 engage the shoulder 108, and the second plurality of protrusions 134 engage a rearward facing shoulder 109. As best shown in FIG. 12, when the high-pressure valve assembly 100 is opened, the valve seal 104 passes through the open end portion 128 and into the hollow interior 122. Therefore, anesthetic agent 60 (represented graphically by fluid flow arrows in FIG. 12) passing through the high-pressure channel 66 is directed around the valve seal 104. More precisely, the anesthetic agent 60 is directed radially outward along the face of end cap 124 and between the second plurality of protrusions 134 (shown in FIG. 11), through the plurality of channels 130 (shown in FIG. 11), radially inward between the first plurality of protrusions 132 (shown in FIG. 11), and then through the reduced diameter portion 106 of the high-pressure channel 66 such that the anesthetic agent 60 does not directly engage the valve seal 104. In this manner, the pressurized anesthetic agent 60 is prevented from pushing the valve seal 104 into engagement with the shoulder 108 and thereby prematurely closing the high-pressure valve assembly 100.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A reservoir for an anesthetic vaporizer comprising:
an open interior;
a high-pressure channel in communication with the open interior, said high-pressure channel configured to transfer an anesthetic agent from a storage container into the open interior when a pressure level within the storage container exceeds a pressure level within the open interior; and
a low-pressure channel in communication with the open interior, said low-pressure channel configured to transfer the anesthetic agent from the storage container into the open interior when the pressure level within the storage container is less than or approximately equal to the pressure level within the open interior;
wherein the low-pressure channel and the high-pressure channel are configured to prevent the open interior from being overfilled with the anesthetic agent under conditions wherein the pressure level within the storage container exceeds the pressure level within the open interior.

2. The reservoir of claim 1, further comprising a low-pressure valve assembly operatively connected to the low-pressure channel, said low-pressure valve assembly configured to selectively occlude the low-pressure channel.

3. The reservoir of claim 2, wherein the low-pressure valve assembly includes a valve spring configured to regulate low-pressure valve assembly actuation.

4. The reservoir of claim 1, further comprising a high-pressure valve assembly operatively connected to the high-pressure channel, said high-pressure valve assembly configured to selectively occlude the high-pressure channel in response to the level of the anesthetic agent within the open interior.

5. The reservoir of claim 4, further comprising a float disposed within the open interior and operatively connected to the high-pressure valve assembly, wherein the float is configured to actuate the high-pressure valve assembly and thereby occlude the high-pressure channel when the anesthetic agent within the open interior reaches a predetermined level.

6. The reservoir of claim 1, further comprising a vapor return tube in communication with the open interior, said vapor return tube configured to transfer an anesthetic vapor from the open interior to the storage container.

7. The reservoir of claim 6, wherein the vapor return tube is aligned with a pitch center of the anesthetic agent within the open interior such that the open interior is prevented from being overfilled with the anesthetic agent when the reservoir is tilted.

8. The reservoir of claim 1, further comprising a discharge tube in communication with the open interior, said discharge tube configured to transfer the anesthetic agent within the open interior to a patient.

9. A reservoir for an anesthetic vaporizer comprising:
an open interior;
a low-pressure channel in communication with the open interior, said low-pressure channel configured to transfer an anesthetic agent from a storage container to the open interior;
a low-pressure device operatively connected to the low-pressure channel, said low-pressure device configured to selectively occlude the low-pressure channel;
a high-pressure channel in communication with the open interior, said high-pressure channel configured to transfer the anesthetic agent from the storage container to the open interior; and
a high-pressure device operatively connected to the high-pressure channel, said high-pressure device configured to selectively occlude the high-pressure channel;
wherein the low-pressure device and the high-pressure device are configured to prevent the open interior from being overfilled with the anesthetic agent under conditions wherein a pressure level within the storage container exceeds a pressure level within the open interior.

10. The reservoir of claim 9, further comprising a vapor return tube in communication with the open interior, said vapor return tube configured to transfer an anesthetic vapor from the open interior to the storage container.

11. The reservoir of claim 10, wherein the vapor return tube is aligned with a pitch center of the anesthetic agent within the open interior such that the open interior is prevented from being overfilled with the anesthetic agent when the reservoir is tilted.

12. The reservoir of claim 9, wherein the low-pressure device includes a low-pressure valve assembly, and the high-pressure device includes a high-pressure valve assembly.

13. The reservoir of claim 12, wherein the low-pressure valve assembly includes a valve spring configured to regulate low-pressure valve assembly actuation.

14. The reservoir of claim 12, further comprising a float disposed within the open interior and operatively connected to the high-pressure valve assembly, wherein the float is configured to actuate the high-pressure valve assembly and thereby occlude the high-pressure channel when the anesthetic agent within the open interior reaches a predetermined level.

15. The reservoir of claim 9, further comprising a discharge tube in communication with the open interior, said discharge tube configured to transfer the anesthetic agent within the open interior to a patient.

16. A method for filling a drug reservoir of an anesthetic vaporizer comprising:
providing a low-pressure channel and a high-pressure channel in communication with an open interior;
transferring anesthetic agent from a storage container, through the low-pressure channel and into the open interior when a pressure level within the storage container is less than or approximately equal to a pressure level within the open interior;
transferring anesthetic agent from the storage container, through the high-pressure channel and into the open interior when the pressure level within the storage container exceeds the pressure level within the open interior portion; and
occluding the high-pressure channel when the anesthetic agent within the open interior reaches a predetermined level.

17. The method of claim 16, further comprising occluding the low-pressure channel when the pressure level within the storage container exceeds the pressure level within the open interior portion.

18. The method of claim 16, further comprising transferring a vaporized anesthetic agent from the open interior to the storage container when the pressure level within the storage container is less than or approximately equal to the pressure level within the open interior.

* * * * *